(12) United States Patent
Shu et al.

(10) Patent No.: US 10,517,474 B2
(45) Date of Patent: Dec. 31, 2019

(54) VENTILATORY LARYNGOSCOPE WITH DISPOSABLE LARYNGOSCOPE LENS

(71) Applicant: Ni Shu, Hohhot (CN)

(72) Inventors: Ni Shu, Hohhot (CN); Rina Wu, Hohhot (CN); Da Ha, Hohhot (CN)

(73) Assignee: Ni Shu, Hohhot, Inner Mongolia (CN)

( * ) Notice: Subject to any disclaimer, the term of this patent is extended or adjusted under 35 U.S.C. 154(b) by 124 days.

(21) Appl. No.: 15/751,016

(22) PCT Filed: Oct. 26, 2016

(86) PCT No.: PCT/CN2016/000584
§ 371 (c)(1),
(2) Date: Feb. 7, 2018

(87) PCT Pub. No.: WO2017/075903
PCT Pub. Date: May 11, 2017

(65) Prior Publication Data
US 2018/0228360 A1    Aug. 16, 2018

(30) Foreign Application Priority Data
Nov. 3, 2015    (CN) .......................... 2015 1 0753521

(51) Int. Cl.
*A61B 1/267*    (2006.01)
*A61B 1/00*    (2006.01)
(Continued)

(52) U.S. Cl.
CPC .......... *A61B 1/267* (2013.01); *A61B 1/00052* (2013.01); *A61B 1/00068* (2013.01); *A61B 1/00091* (2013.01); *A61B 1/00105* (2013.01); *A61B 1/00137* (2013.01); *A61B 1/015* (2013.01); *A61B 1/05* (2013.01);
(Continued)

(58) Field of Classification Search
CPC ...... A61B 1/267; A61B 1/2673; A61B 1/2676
See application file for complete search history.

(56) References Cited

U.S. PATENT DOCUMENTS 10,194,791 B2 *    2/2019   McGrath ................ A61B 1/267
2002/0022769 A1 *  2/2002   Smith ................ A61B 1/00052
                                                                600/188
(Continued)

*Primary Examiner* — Eric S Gibson
(74) *Attorney, Agent, or Firm* — Oliff PLC

(57) ABSTRACT

A ventilatory laryngoscope with disposable laryngoscope lens including: a laryngoscope handle and a laryngoscope lens that is connected with an extension arm of the handle; transparent lens protecting cover on the end of the lens cavity; oxygen injecting through-hole on the cover; oxygen supply pipe in seal plug connection with the through-hole, the other end connected with an oxygen source pipe; scrubbing nozzle on the cover, and a drug delivery pipe. The laryngoscope has advantages: during the trachea intubation, ventilation and oxygen supply may be achieved in the body to effectively prevent cerebral anoxia and prolong the safe time limit of the intubation, improve the success rate of cardio-pulmonary resuscitation, and provide a safe and reliable guarantee; improve intubation safety and reduce professional risk; the secreta may be removed from the cover to achieve timely rescue of critically ill patients by collecting clear glottis image and smoothly completing the intubation.

12 Claims, 14 Drawing Sheets

(51) Int. Cl.
  *A61B 1/015* (2006.01)
  *A61B 1/12* (2006.01)
  *A61M 16/04* (2006.01)
  *A61B 1/06* (2006.01)
  *A61M 16/14* (2006.01)
  *A61B 1/05* (2006.01)

(52) U.S. Cl.
  CPC ............ *A61B 1/0684* (2013.01); *A61B 1/126* (2013.01); *A61B 1/127* (2013.01); *A61M 16/0488* (2013.01); *A61M 16/14* (2013.01); *A61B 1/00103* (2013.01); *A61M 2205/502* (2013.01); *A61M 2209/10* (2013.01)

(56) References Cited

U.S. PATENT DOCUMENTS

| | | | |
|---|---|---|---|
| 2006/0063973 A1* | 3/2006 | Makower | A61B 1/00135 600/114 |
| 2013/0023729 A1* | 1/2013 | Vazales | A61B 1/0669 600/104 |
| 2013/0057667 A1* | 3/2013 | McGrath | A61B 1/00052 348/65 |
| 2015/0366445 A1* | 12/2015 | Rutgers | A61B 1/267 600/120 |
| 2016/0345803 A1* | 12/2016 | Mallory | A61B 1/00068 |
| 2017/0258550 A1* | 9/2017 | Vazales | A61B 1/00068 |
| 2018/0064896 A1* | 3/2018 | Kleene | A61B 1/01 |
| 2018/0098692 A1* | 4/2018 | Cantrell | A61B 1/267 |
| 2018/0146839 A1* | 5/2018 | Friedlander | A61B 34/30 |
| 2018/0206705 A1* | 7/2018 | Chan | A61B 1/00048 |
| 2018/0214013 A1* | 8/2018 | Casson | A61B 1/015 |
| 2018/0221610 A1* | 8/2018 | Larson | A61B 1/00009 |
| 2018/0228360 A1* | 8/2018 | Shu | A61B 1/00052 |
| 2018/0344410 A1* | 12/2018 | Krimsky | A61B 34/10 |
| 2019/0142262 A1* | 5/2019 | Inglis | A61B 1/267 600/188 |
| 2019/0192163 A1* | 6/2019 | Vasquez | A61B 17/12104 |

* cited by examiner

US 10,517,474 B2

VENTILATORY LARYNGOSCOPE WITH DISPOSABLE LARYNGOSCOPE LENS

FIELD OF INVENTION

This invention relates to a laryngoscope, particularly to a ventilatory laryngoscope with disposable laryngoscope lens.

BACKGROUND OF INVENTION

An anesthetic pharyngoscope is the preferred medical equipment for trachea intubation glottis display during general anesthesia induction and cardio-pulmonary resuscitation. The laryngoscope lens of the anesthetic pharyngoscope is mostly reused but the anesthetic pharyngoscope with disposable laryngoscope lens is gradually used to avoid the cross infection of patients resulting from improper disinfection during refuse. However, existing ventilatory laryngoscope with disposable laryngoscope lens has disadvantage: due to its simple function: it cannot be used for the patient for which airway intubation is difficult, and it is possible to aggravate the oxygen deficit in the visceral organs, such as brain, heart, kidney, of the patients with high throat, short neck, protruded upper teeth due to insufficient ventilation and oxygen supply during intubation, obesity and other difficult intubation patients. In the academic circle, intubation completion time is clearly limited for the patient suffering from respiratory failure or respiratory arrest (15-20 s), and for this time limit, it is difficult for well-trained senior anesthetist to complete anesthesia within specified safety time in case of intubation difficulty, endangering the patient or causing rescue failed.

Additionally, the existing anesthetic pharyngoscope with disposable laryngoscope lens has no atomization anesthesia function, and only is used for inspecting displayed glottis, and suffocation and threat to life may be caused by failure to slack glottis and reduce the stress reaction of intubation due to no atomization anesthesia of the glottis; the rescue is not achieved due to failure to fully meet the above time limit requirement. At the same time, intravenous administration cannot be achieved due to difficulty in venepuncture during cardio-pulmonary resuscitation at the site, existing disposable laryngoscope lens has no function to deliver atomizing cardio-pulmonary resuscitation drug by trachea, such as epinephrine, atropine and other first-aid drug. Therefore, the purpose of rescue seriously ill patient by endotracheal administration is not achieved. (the endotracheal administration has same absorption rate with intravenous administration).

If the transparent protective cover of the lens is covered by oral hemorrhage, vomitus and other secreta of the patient, video image cannot be collected or the glottis cannot be clearly observed by existing disposable laryngoscope lens, impacting smooth completion of intubation, and delaying in rescue.

The first purpose according to this invention is to provide a disposable laryngoscope lens which can achieve ventilation and oxygen supply for the patient together with the anesthetic pharyngoscope while displaying the glottis during trachea intubation.

The first purpose according to this invention is to provide the technical solution shown as follows: A ventilatory laryngoscope with disposable laryngoscope lens comprises a laryngoscope handle and a laryngoscope lens, which is characterized in that the laryngoscope lens is movably connected with the extension arm on the end of the laryngoscope handle, the extension arm is arranged in a laryngoscope lens cavity, a transparent lens protecting cover is arranged on the end surface of the closed end of the front end of the laryngoscope lens cavity, an oxygen injecting through-hole is formed on the transparent lens protecting cover; an oxygen supply pipe extends from the laryngoscope handle cavity to extension arm tail end along the top of the laryngoscope handle; also the oxygen supply pipe is fixed on the top of the extension arm from the extension arm tail end to the extension arm cavity, and in seal plug connection with the oxygen injecting through-hole, or the oxygen supply pipe is fixed from the extension arm cavity to the top of the extension arm along the extension arm tail end, and in seal plug connection with the oxygen injecting through-hole, and another end of the oxygen supply pipe is connected with or inserted into an oxygen source pipe;

The ventilatory laryngoscope is provided with the disposable laryngoscope lens comprising a disposable laryngoscope lens body, at tongue depressor and the laryngoscope lens cavity; the laryngoscope lens body is straight or bent, a fixing lug or a buckle is arranged on the tail end of the laryngoscope lens body, the fixing lug or the buckle is movably buckled with the slot of the extension arm tail end; the tongue depressor is connected with the front end of the laryngoscope lens body, the laryngoscope lens cavity is located in the laryngoscope lens body, the end port of the tail end of the laryngoscope lens cavity is open, the end port of the front end of the laryngoscope lens cavity is closed, and the transparent lens protecting cover is arranged on the end surface of the closed end port of the front end of the laryngoscope lens cavity.

The ventilatory laryngoscope is provided with disposable laryngoscope lens comprising a light source on the top of the extension arm, and the light source is arranged on the inner side of the transparent lens protecting cover.

The ventilatory laryngoscope is provided with disposable laryngoscope lens comprising an oxygen supply solenoid valve on the oxygen supply pipe in the laryngoscope handle; or the oxygen supply solenoid valve is arranged on the any part of the oxygen source pipe.

The ventilatory laryngoscope is provided with disposable laryngoscope lens comprising a display screen on the laryngoscope handle, a camera electrically connected with the display screen is arranged on the top of the extension arm, and the camera is installed on the inner side of the transparent lens protecting cover.

The ventilatory laryngoscope is provided with disposable laryngoscope lens comprising a scrubbing nozzle on the transparent lens protecting cover; an expiratory air removal nozzle is arranged in the laryngoscope handle, one end of the expiratory air removal nozzle is connected with an oxygen source, another end of the expiratory air removal nozzle is inserted and fixed on the top of the extension arm, and in sealed and movable connection with the scrubbing nozzle, the opening of the scrubbing nozzle aligns with the mirror surface of the transparent lens protecting cover.

The ventilatory laryngoscope is provided with disposable laryngoscope lens comprising a scrubbing control valve on the expiratory air removal nozzle, the scrubbing control valve is arranged on the laryngoscope handle, and the scrubbing control valve is interlock control with the oxygen supply solenoid valve. When the scrubbing control valve is opened, the oxygen supply solenoid valve is closed, when the oxygen supply solenoid valve is opened, the scrubbing control valve is closed.

The ventilatory laryngoscope with disposable laryngoscope lens further comprises a drug delivery pipe, a drug delivery control valve is installed on the drug delivery pipe, the drug delivery control valve is arranged on the laryngoscope handle, one end of the drug delivery pipe is connected with a drug barrel in the laryngoscope handle, and another end of the drug delivery pipe is fixed on the top of the extension arm along the extension arm tail end; a atomizer head is arranged on the transparent lens protecting cover, an air inlet and a drug inlet on the atomizer head are respectively in sealed and movable connection with the drug delivery pipe and the oxygen supply pipe fixed on the top of the extension arm. The drug delivery control valve and the oxygen supply solenoid valve are separately controlled.

The second purpose of this invention is to provide a disposable laryngoscope lens for displaying the glottis together with the anesthetic pharyngoscope while supplying oxygen during trachea intubation, and a ventilatory laryngoscope with disposable laryngoscope lens having scrubbing function.

The second purpose of this invention is achieved by the following technical solution: the ventilatory laryngoscope comprises a laryngoscope handle and a laryngoscope lens, and is characterized in that the laryngoscope lens is movably connected with the extension arm on the end of the laryngoscope handle, the extension arm is arranged in the laryngoscope lens cavity, and a transparent lens protecting cover is arranged on the closed port of the front end of the laryngoscope lens cavity, and an oxygen injecting through-hole is formed on the transparent lens protecting cover; the oxygen supply pipe extends from the laryngoscope handle cavity to the extension arm tail end along the top of the laryngoscope handle; also the oxygen supply pipe is fixed on the top of the extension arm from the extension arm tail end to the extension arm cavity, and in seal plug connection with the oxygen injecting through-hole, or the oxygen supply pipe is fixed from the extension arm cavity to the top of the extension arm along the extension arm tail end, and in seal plug connection with the oxygen injecting through-hole, and another end of the oxygen supply pipe is connected with or inserted into an oxygen source pipe; a scrubbing nozzle is arranged on the transparent lens protecting cover; an expiratory air removal nozzle is arranged in the laryngoscope handle, one end of the expiratory air removal nozzle is connected with an oxygen source, another end of the expiratory air removal nozzle is inserted and fixed on the top of the extension arm, and in sealed and movable connection with the scrubbing nozzle, the opening of the scrubbing nozzle aligns with the mirror surface of the transparent lens protecting cover.

The ventilatory laryngoscope with disposable laryngoscope lens having scrubbing function comprises a disposable laryngoscope lens body, a tongue depressor and a laryngoscope lens cavity; the laryngoscope lens body is straight or bent; a fixing lug or a buckle is arranged on the tail end of the laryngoscope lens body, the fixing lug or the buckle is movably buckled with the slot of the extension arm tail end; the tongue depressor is connected with the front end of the laryngoscope lens body, the laryngoscope lens cavity is located in the laryngoscope lens body, the end port of the tail end of the laryngoscope lens cavity is open, the end port of the front end of the laryngoscope lens cavity is closed, and the transparent lens protecting cover is arranged on the end surface of the closed end port of the front end of the laryngoscope lens cavity.

The ventilatory laryngoscope with disposable laryngoscope lens having scrubbing function comprises a light source on the top of the extension arm, and the light source is arranged on the inner side of the transparent lens protecting cover.

The ventilatory laryngoscope with disposable laryngoscope lens having scrubbing function comprises an oxygen supply solenoid valve on the oxygen supply pipe in the laryngoscope handle; or the oxygen supply solenoid valve is arranged on the any part of the oxygen source pipe.

The ventilatory laryngoscope with disposable laryngoscope lens having scrubbing function comprises a display screen on the laryngoscope handle, a camera electrically connected with the display screen is arranged on the top of the extension arm, and the camera is installed on the inner side of the transparent lens protecting cover.

The ventilatory laryngoscope with disposable laryngoscope lens having scrubbing function comprises a scrubbing control valve on the expiratory air removal nozzle, the scrubbing control valve is arranged on the laryngoscope handle, and the scrubbing control valve is interlock control with the oxygen supply solenoid valve. When the scrubbing control valve is opened, the oxygen supply solenoid valve is closed, when the oxygen supply solenoid valve is opened, the scrubbing control valve is closed.

The ventilatory laryngoscope with disposable laryngoscope lens having scrubbing function further comprises a drug delivery pipe, a drug delivery control valve is installed on the drug delivery pipe, the drug delivery control valve is arranged on the laryngoscope handle, one end of the drug delivery pipe is connected with a drug barrel in the laryngoscope handle, and another end of the drug delivery pipe is fixed on the top of the extension arm along the extension arm tail end; a atomizer head is arranged on the transparent lens protecting cover, an air inlet and a drug inlet on the atomizer head are respectively in sealed and movable connection with the drug delivery pipe and the oxygen supply pipe fixed on the top of the extension arm. The drug delivery control valve and the oxygen supply solenoid valve are separately controlled.

The third purpose of this invention is to provide a disposable laryngoscope lens for displaying the glottis together with the anesthetic pharyngoscope while delivering drug and supplying oxygen during trachea intubation, and a drug-delivering ventilatory laryngoscope with disposable laryngoscope lens with scrubbing function.

The third purpose of this invention is achieved by the following technical solution: the ventilatory laryngoscope comprises a laryngoscope handle and a laryngoscope lens, the end of the laryngoscope lens is movably connected with the extension arm, the extension arm is arranged in the laryngoscope lens cavity, and a transparent lens protecting cover is arranged on the closed port of the front end of the laryngoscope lens cavity, and an oxygen injecting through-hole is formed on the transparent lens protecting cover; the oxygen supply pipe extends from the laryngoscope handle cavity to the extension arm tail end along the top of the laryngoscope handle; also the oxygen supply pipe is fixed on the top of the extension arm from the extension arm tail end to the extension arm cavity, and in seal plug connection with the oxygen injecting through-hole, or the oxygen supply pipe is fixed from the extension arm cavity to the top of the extension arm along the extension arm tail end, and in seal plug connection with the oxygen injecting through-hole, and another end of the oxygen supply pipe is connected with or inserted into an oxygen source pipe; a scrubbing nozzle is arranged on the transparent lens protecting cover; an expiratory air removal nozzle is arranged in the laryngoscope handle, one end of the expiratory air removal nozzle is connected with an oxygen source, another end of the expiratory air removal nozzle is inserted and fixed on the top of the extension arm, and in sealed and movable connection with the scrubbing nozzle, the opening of the scrubbing nozzle aligns with the mirror surface of the transparent lens protecting cover. The ventilatory laryngoscope further comprises a drug delivery pipe, a drug delivery control valve is installed on the drug delivery pipe, the drug delivery control valve is arranged on the laryngoscope handle, one end of the drug delivery pipe is connected with a drug barrel in the laryngoscope handle, and another end of the drug delivery pipe is fixed on the top of the extension arm along the extension arm tail end; a atomizer head is arranged on the transparent lens protecting cover, an air inlet and a drug inlet on the atomizer head are respectively in sealed and movable connection with the drug delivery pipe and the oxygen supply pipe fixed on the top of the extension arm. The drug delivery control valve and the oxygen supply solenoid valve are separately controlled.

The drug-delivering ventilatory laryngoscope with disposable laryngoscope lens having scrubbing function comprises a disposable laryngoscope lens body, a tongue depressor, a laryngoscope lens cavity; the laryngoscope lens body is straight or bent, a fixing lug or a buckle is arranged on the tail end of the laryngoscope lens body, the fixing lug or the buckle is movably buckled with the slot of the extension arm tail end; the tongue depressor is connected with the front end of the laryngoscope lens body, the laryngoscope lens cavity is located in the laryngoscope lens body, the end port of the tail end of the laryngoscope lens cavity is open, the end port of the front end of the laryngoscope lens cavity is closed, and the transparent lens protecting cover is arranged on the end surface of the closed end port of the front end of the laryngoscope lens cavity.

The drug-delivering ventilatory laryngoscope with disposable laryngoscope lens having scrubbing function comprises a light source on the top of the extension arm, and the light source is arranged on the inner side of the transparent lens protecting cover.

The drug-delivering ventilatory laryngoscope with disposable laryngoscope lens having scrubbing function comprises an oxygen supply solenoid valve on the oxygen supply pipe in the laryngoscope handle; or the oxygen supply solenoid valve is arranged on the any part of the oxygen source pipe.

The drug-delivering ventilatory laryngoscope with disposable laryngoscope lens having scrubbing function comprises display screen on the laryngoscope handle, a camera electrically connected with the display screen is arranged on the top of the extension arm, and the camera is installed on the inner side of the transparent lens protecting cover.

The drug-delivering ventilatory laryngoscope with disposable laryngoscope lens having scrubbing function comprises a scrubbing control valve on the expiratory air removal nozzle, the scrubbing control valve is arranged on the laryngoscope handle, and the scrubbing control valve is interlock control with the oxygen supply solenoid valve. When the scrubbing control valve is opened, the oxygen supply solenoid valve is closed, when the oxygen supply solenoid valve is opened, the scrubbing control valve is closed.

The fourth purpose of this invention is to provide a disposable laryngoscope lens for displaying the glottis together with the anesthetic pharyngoscope while collecting glottis image by video, delivering drug, and supplying oxygen during trachea intubation, and a drug-delivering ventilatory video laryngoscope with disposable laryngoscope lens having scrubbing function.

The purpose of this invention is achieved by the following technical solution: the drug-delivering ventilatory video laryngoscope with disposable laryngoscope lens having scrubbing function comprises a laryngoscope handle and a laryngoscope lens, the laryngoscope lens is movably connected with the extension arm on the end of the laryngoscope lens, the extension arm is arranged in the laryngoscope lens cavity, and a transparent lens protecting cover is arranged on the closed port of the front end of the laryngoscope lens cavity, and an oxygen injecting through-hole is formed on the transparent lens protecting cover; the oxygen supply pipe extends from the laryngoscope handle cavity to the extension arm tail end along the top of the laryngoscope handle; also the oxygen supply pipe is fixed on the top of the extension arm from the extension arm tail end to the extension arm cavity, and in seal plug connection with the oxygen injecting through-hole, or the oxygen supply pipe is fixed from the extension arm cavity to the top of the extension arm along the extension arm tail end, and in seal plug connection with the oxygen injecting through-hole, and another end of the oxygen supply pipe is connected with or inserted into an oxygen source pipe;

A scrubbing nozzle is arranged on the transparent lens protecting cover; an expiratory air removal nozzle is arranged in the laryngoscope handle, one end of the expiratory air removal nozzle is connected with an oxygen source, another end of the expiratory air removal nozzle is inserted and fixed on the top of the extension arm, and in sealed and movable connection with the scrubbing nozzle, the opening of the scrubbing nozzle aligns with the mirror surface of the transparent lens protecting cover.

The drug-delivering ventilatory video laryngoscope with disposable laryngoscope lens having scrubbing function further comprises a drug delivery pipe, a drug delivery control valve is installed on the drug delivery pipe, the drug delivery control valve is arranged on the laryngoscope handle, one end of the drug delivery pipe is connected with a drug barrel in the laryngoscope handle, and another end of the drug delivery pipe is fixed on the top of the extension arm along the extension arm tail end; a atomizer head is arranged on the transparent lens protecting cover, an air inlet and a drug inlet on the atomizer head are respectively in sealed and movable connection with the drug delivery pipe and the oxygen supply pipe fixed on the top of the extension arm. The drug delivery control valve and the oxygen supply solenoid valve are separately controlled.

The ventilatory laryngoscope comprises a display screen on the laryngoscope handle, a camera electrically connected with the display screen is arranged on the top of the extension arm, and the camera is installed on the inner side of the transparent lens protecting cover.

The drug-delivering ventilatory video laryngoscope with disposable laryngoscope lens having scrubbing function comprises a disposable laryngoscope lens body, a tongue depressor and a laryngoscope lens cavity; the laryngoscope lens body is straight or bent; a fixing lug or a buckle is arranged on the tail end of the laryngoscope lens body, the fixing lug or the buckle is movably buckled with the slot of the extension arm tail end; the tongue depressor is connected with the front end of the laryngoscope lens body, the laryngoscope lens cavity is located in the laryngoscope lens body, the end port of the tail end of the laryngoscope lens cavity is open, the end port of the front end of the laryngoscope lens cavity is closed, and the transparent lens protecting cover is arranged on the end surface of the closed end port of the front end of the laryngoscope lens cavity.

The drug-delivering ventilatory video laryngoscope with disposable laryngoscope lens having scrubbing function comprises an oxygen supply solenoid valve on the oxygen supply pipe in the laryngoscope handle; or the oxygen supply solenoid valve is arranged on the any part of the oxygen source pipe.

The drug-delivering ventilatory video laryngoscope with disposable laryngoscope lens having scrubbing function comprises a scrubbing control valve on the expiratory air removal nozzle, the scrubbing control valve is arranged on the laryngoscope handle, and the scrubbing control valve is interlock control with the oxygen supply solenoid valve. When the scrubbing control valve is opened, the oxygen supply solenoid valve is closed, when the oxygen supply solenoid valve is opened, the scrubbing control valve is closed.

This invention has the following advantages: (1) during the trachea intubation ventilation and oxygen supply may be achieved in the body to rapidly rise oxygen partial pressure, prevent cerebral anoxia, improve the success rate of cardio-pulmonary resuscitation, and provide safe and reliable guarantee; (2) in case of difficulty in intubation due to high throat, short neck, protruded upper teeth, backward tongue root movement, obesity and other difficult intubation patients, oxygen supply may be achieved for the patient to effectively prolong the safe time limit of the trachea intubation, improve intubation safety and reduce the professional risk of the intubation; (3) during rescue of newborn for emergency asphyxia, the straight ventilatory laryngoscope with disposable laryngoscope lens has obvious advantages, the intubation for the newborn is more difficult than the intubation for the adult due to physiologic-anatomical features of the newborn, such as large head, thin shoulder, U epiglottis, higher throat position in $3^{rd}$-$4^{th}$ cervical vertebra, funnel-shaped trachea, improving the difficulty in intubation for the newborn; according to the statistics of WHO, the newborns died for asphyxia are about ¾ of more than 4 million newborns died every year, and additionally more than 1 million newborns suffer from cerebral palsy, learning disabilities, and other disabilities for asphyxia during labor, and the neonatal asphyxia is the second cause of death for less than 5 years old children in China; the newborns have same safe intubation time limit with the adult (15-20 s), improving the difficulty and sense of urgency of newborn resuscitation; the ventilatory laryngoscope with disposable laryngoscope lens can achieve ventilation and oxygen supply for the newborn within the first time during asphyxia intubation, changes the oxygen-free intubation into the ventilation and oxygen supply intubation to prolong the safe time limit of the trachea intubation, provide a strong guarantee for preventing the cerebral anoxia of the newborn, and effectively reduce the death rate and cerebral palsy, mentally handicapped and disability morbidity.

(4) During the trachea intubation, when it is impossible to complete video image collection or clearly observe glottis due to covering the transparent protecting cover of the camera with blood, vomitus and other secreta in the mouth of the patient, the ventilatory laryngoscope with disposable laryngoscope lens having scrubbing function may timely remove the secreta from the transparent protecting cover to achieve timely rescue of critically ill patients by collecting clear glottis image and smoothly completing the intubation.

(5) Also, this invention has a function to deliver cardio-pulmonary resuscitation drug and perform glottis anesthesia by the trachea. When intravenous administration is not achieved due to the difficulty in venipuncture during onsite rescue of the critically ill patients by cardio-pulmonary resuscitation, the laryngoscope according to this invention may deliver atropine, epinephrine and other first-aid drugs by the trachea to achieve rescue of the critically ill patients against time by rapid drug delivery (the endotracheal administration has same absorption rate with intravenous administration). At the same time, when the life of the critically ill patient due to glottis closure resulting from laryngospasm, atomizing anesthesia may be immediately performed for the glottis to slack the glottis, reduce the stress reaction of intubation, facilitate smooth completion of the intubation, and timely and effective rescue the critically ill patient.

DESCRIPTION ON FIGURES

Figure 1:
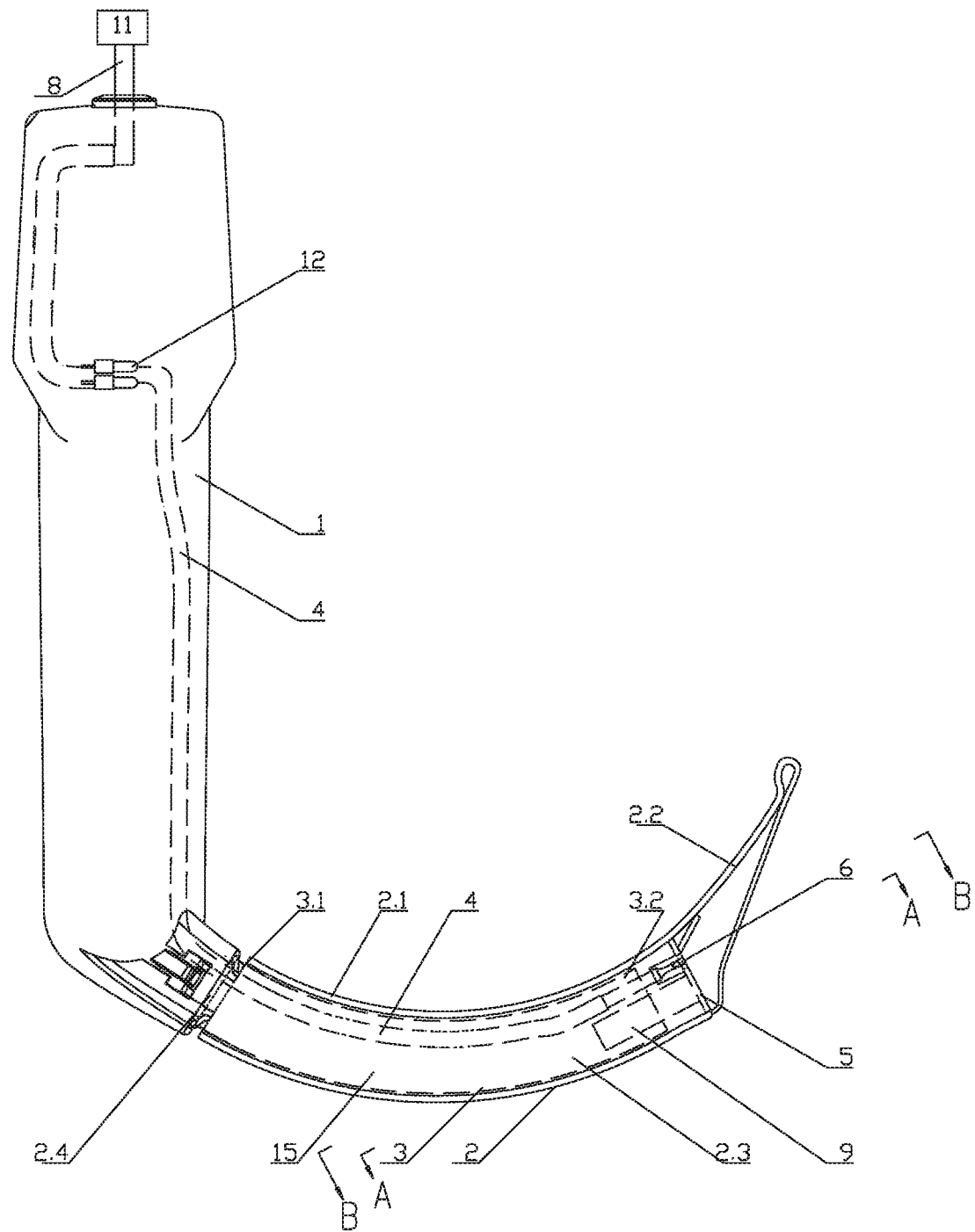
FIG. 1 show the schematic diagram for the whole structure of the ventilatory laryngoscope with disposable laryngoscope lens.
Figure 2:
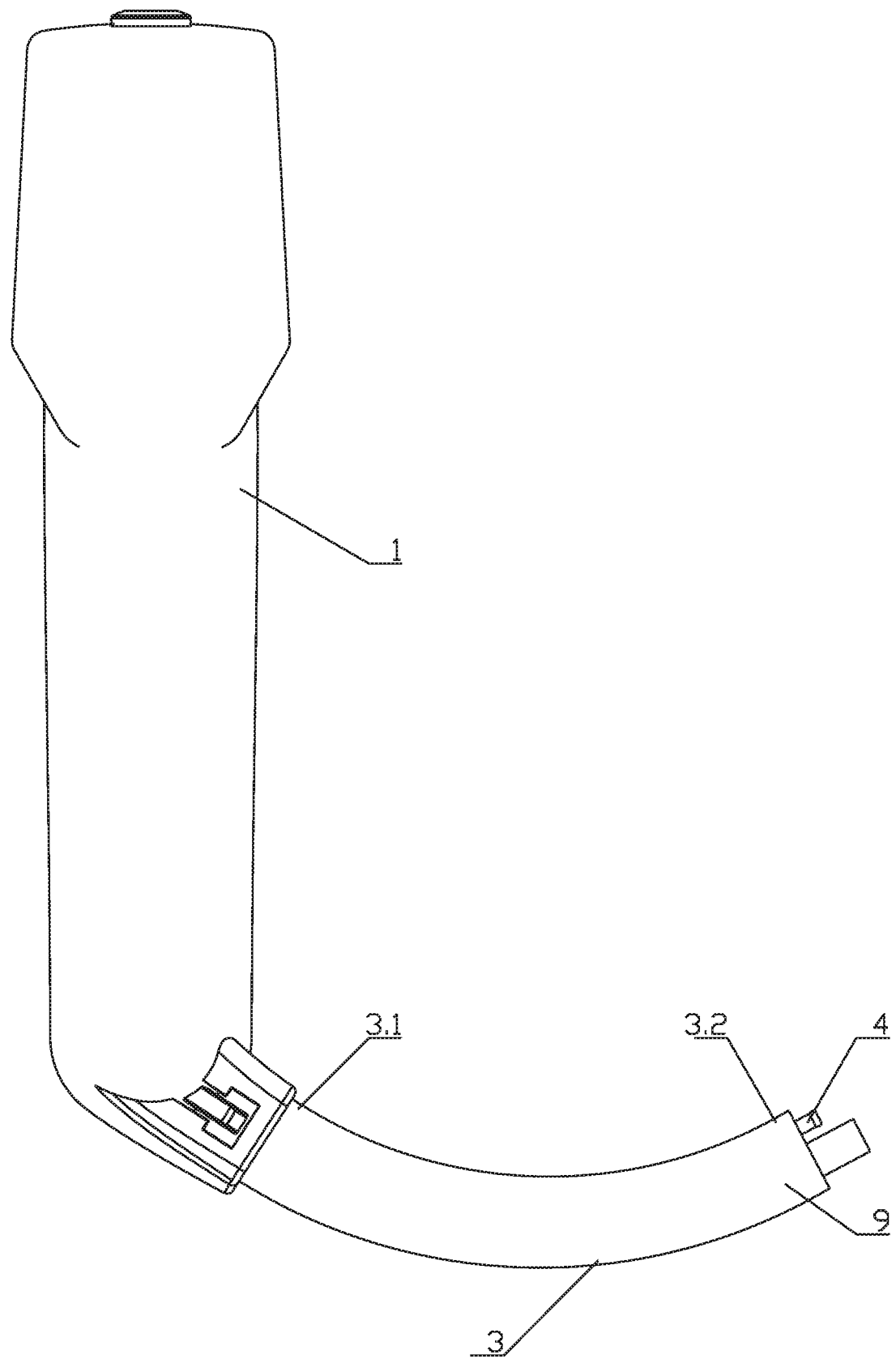
FIG. 2 shows the show the schematic diagram for the whole structure of the laryngoscope handle.
Figure 3:
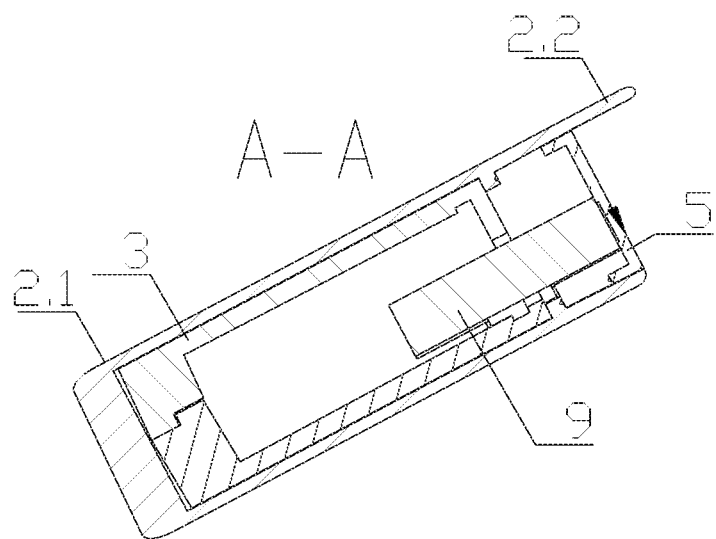
FIG. 3 shows the schematic diagram for section A-A shown in FIG. 1.
Figure 4:
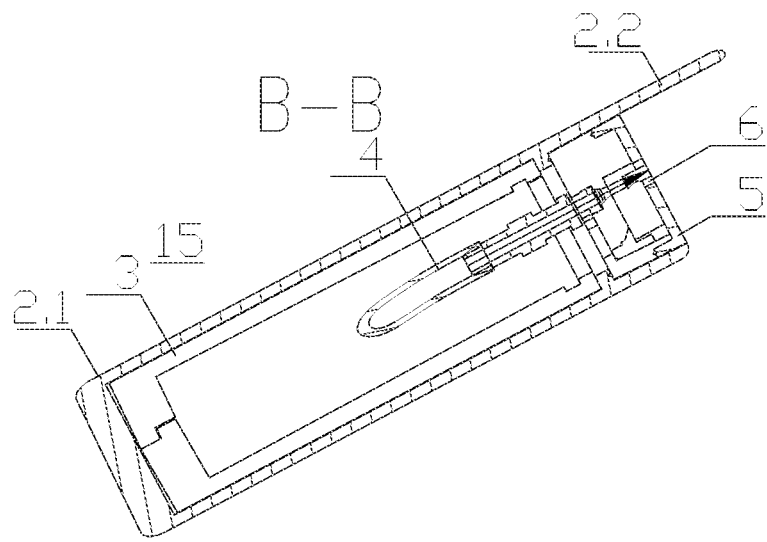
FIG. 4 shows the schematic diagram for section B-B shown in FIG. 1.

laryngoscope handle 1, laryngoscope lens 2, laryngoscope lens body 2.1, tongue depressor 2.2, laryngoscope lens cavity 2.3, tail end port of laryngoscope lens cavity 2.3.1, closed port of front end of laryngoscope lens cavity 2.3.2, fixing lug or buckle 2.4, extension arm 3, extension arm tail end 3.1, top of extension arm 3.2, oxygen supply pipe 4, transparent lens protecting cover 5, oxygen injecting through-hole 6, camera 7, oxygen source pipe 8, light source 9, display screen 10, oxygen source 11, oxygen supply solenoid valve 12, scrubbing control valve 13, scrubbing nozzle 14, expiratory air removal nozzle 15, drug delivery pipe 16, drug delivery control valve 17, drug barre 118, atomizer head 19, air inlet 20, drug inlet 21.

MODE OF CARRYING OUT INVENTION

Embodiment 1 as shown in FIG. 1 to FIG. 4, the ventilatory laryngoscope with disposable laryngoscope lens 2 comprises a laryngoscope handle 1 and a laryngoscope lens 2, the laryngoscope lens 2 is movably connected with the extension arm 3 on the end of the laryngoscope handle 1, the extension arm 3 is arranged in a laryngoscope lens cavity 2.3, a transparent lens protecting cover 5 is arranged on the end surface of the closed end of the front end of the laryngoscope lens cavity 2.3, an oxygen injecting through-hole 6 is formed on the transparent lens protecting cover 5; an oxygen supply pipe 4 extends from the laryngoscope handle cavity to extension arm tail end 3.1 along the top of the laryngoscope handle 1; also the oxygen supply pipe 4 is fixed on the top 3.2 of the extension arm from the extension arm tail end 3.1 to the cavity of the extension arm 3, and in seal plug connection with the oxygen injecting through-hole 6, and another end is connected with or inserted into an oxygen source pipe 8, and an oxygen supply solenoid valve 12 is arranged on the oxygen supply pipe 4 in the laryngoscope handle 1.

Figure 5:
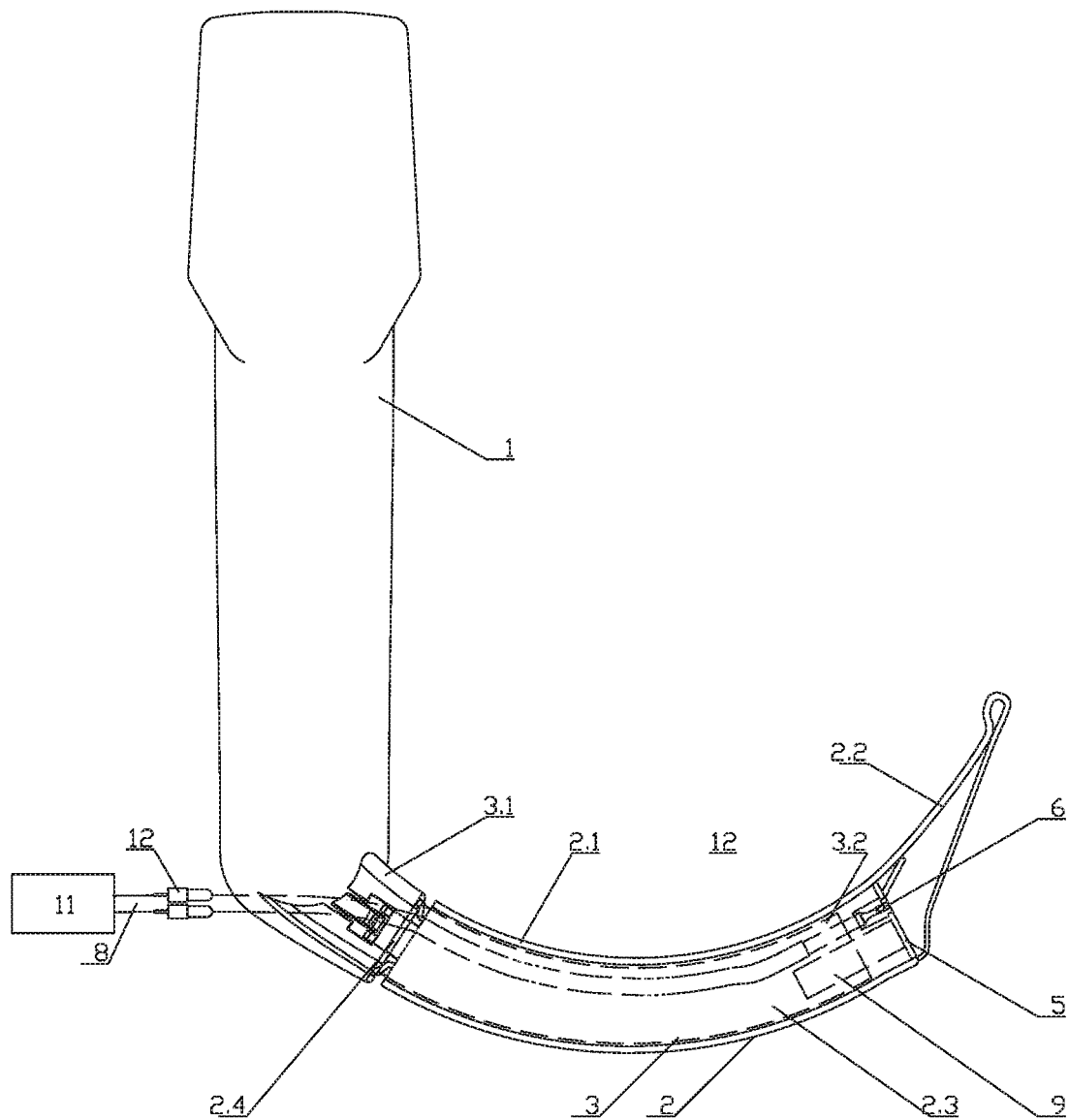
FIG. 5 shows the schematic diagram for the whole structure of another embodiment of the ventilatory laryngoscope with disposable laryngoscope lens according to Embodiment 1.

As shown in FIG. 5, in another solution for the above structure, the oxygen supply pipe 4 is fixed from the extension arm cavity to the top 3.2 of the extension arm along the extension arm tail end 3.1, and in seal plug connection with the oxygen injecting through-hole 6, another end is connected with or inserted into an oxygen source pipe 8, and the oxygen supply solenoid valve 12 is arranged on any part of the oxygen supply pipe 4.

The light source 9 is arranged on the top of the extension arm 3, and the light source 9 is installed in the transparent lens protecting cover 5. Another solution may be used.

Figure 6:
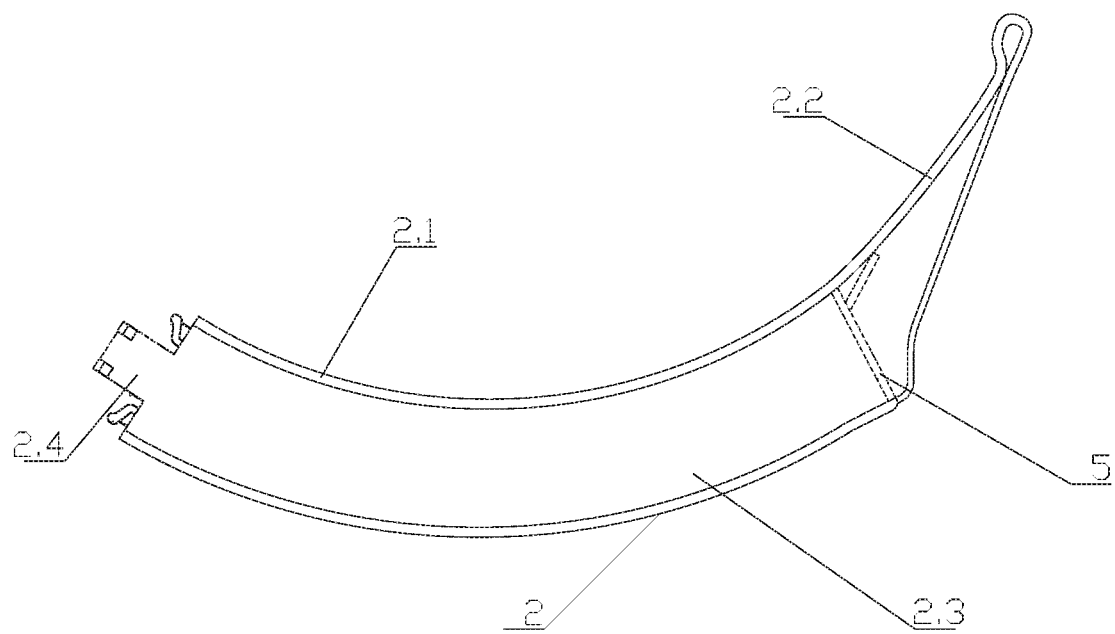
FIG. 6 shows the schematic diagram for the whole structure of the laryngoscope lens according to Embodiment 1.

As shown in FIG. 6, the laryngoscope lens 2 comprises a disposable laryngoscope lens body 2.1, a tongue depressor 2.2 and a laryngoscope lens cavity 2.3; the laryngoscope lens body 2.1 is straight or bent, a fixing lug or a buckle 2.4 is arranged on the tail end of the laryngoscope lens body 2.1, the fixing lug or the buckle 2.4 is movably buckled with the slot of the extension arm tail end 3.1; the tongue depressor 2.2 is connected with the front end of the laryngoscope lens body 2.1, the laryngoscope lens cavity 2.3 is located in the laryngoscope lens body 2.1, the end port 2.3.1 of the tail end of the laryngoscope lens cavity 2.3 is open, the end port 2.3.2 of the front end of the laryngoscope lens cavity 2.3 is closed, and the transparent lens protecting cover 5 is arranged on the end surface of the closed end port 2.3.2 of the front end of the laryngoscope lens cavity 2.3.

Embodiment 2

Figure 7:
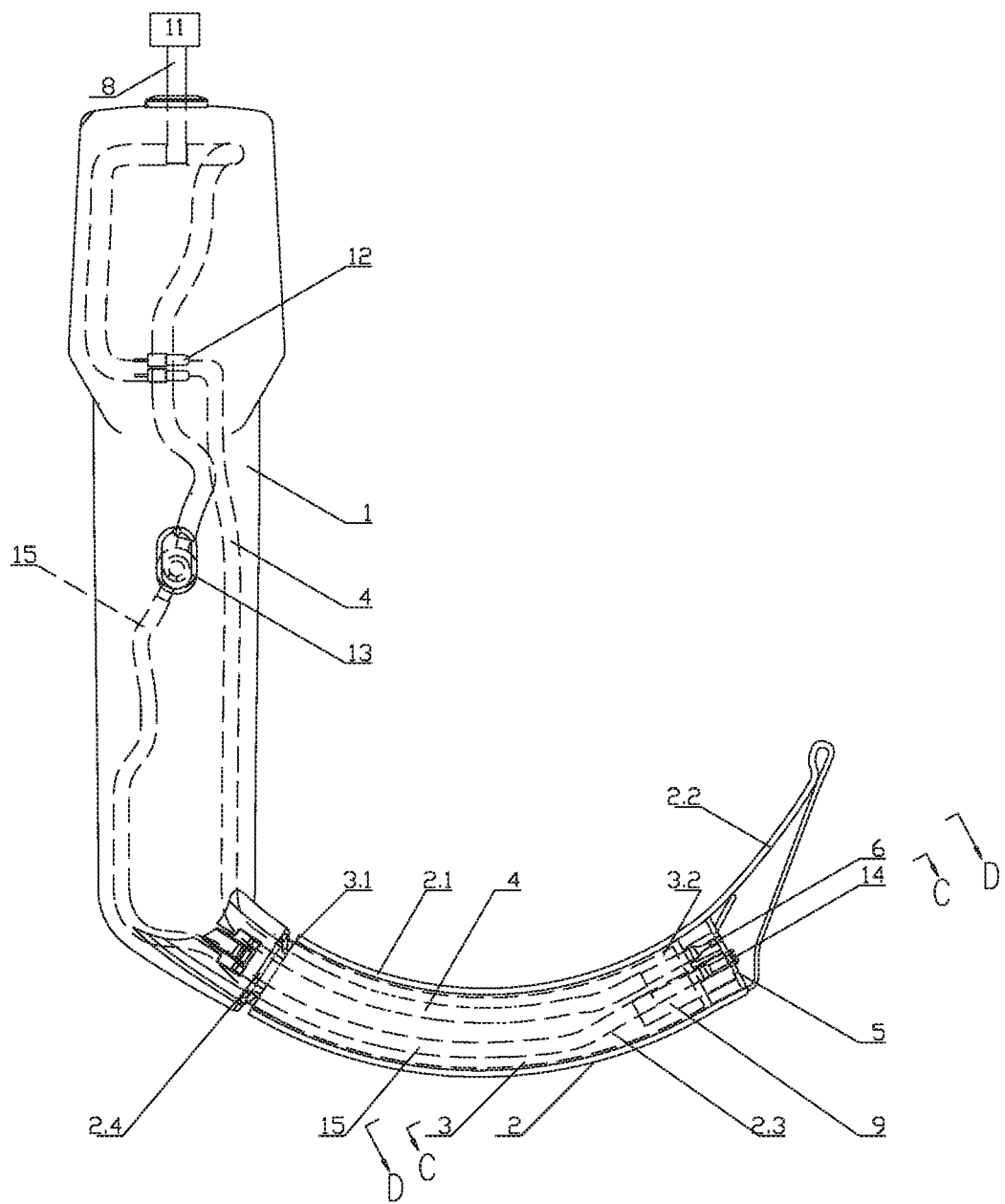
FIG. 7 shows the schematic diagram for the whole structure of the ventilatory laryngoscope with disposable laryngoscope lens having scrubbing function according to Embodiment 2.
Figure 8:
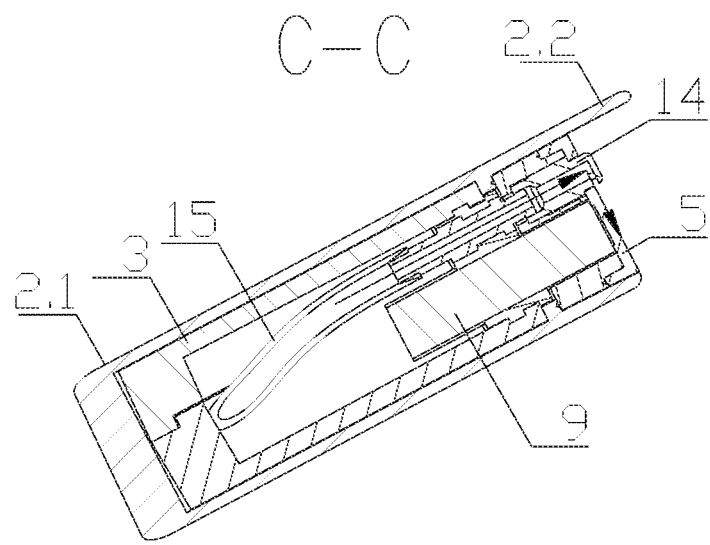
FIG. 8 shows the schematic diagram for section C-C shown in FIG. 7.
Figure 9:
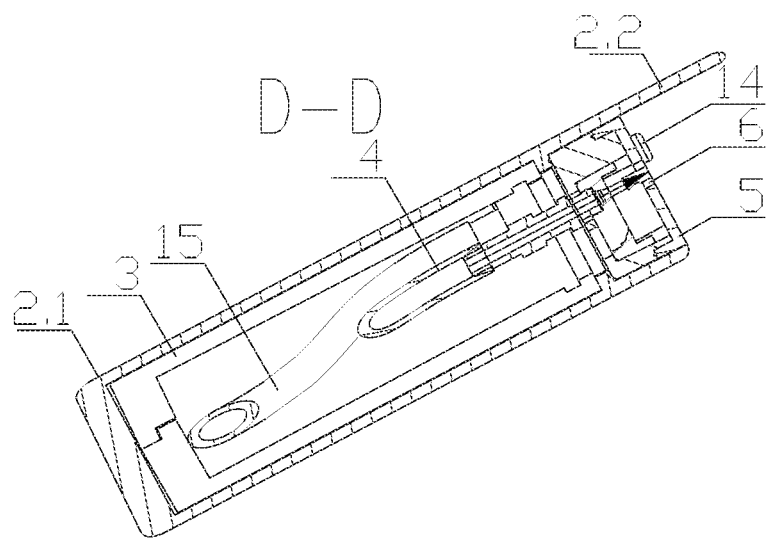
FIG. 9 shows the schematic diagram for section D-D shown in FIG. 7.

FIGS. 7-9 show the ventilatory laryngoscope with disposable laryngoscope lens having scrubbing function, other structure of which is shown in Embodiment 1; a scrubbing nozzle 14 is arranged on the transparent lens protecting cover 5; an expiratory air removal nozzle 15 is arranged in the laryngoscope handle 1, one end of the expiratory air removal nozzle 15 is connected with an oxygen source 11, another end of the expiratory air removal nozzle 15 is inserted from the extension arm tail end 3.1 and fixed on the top 3.2 of the extension arm 3, and in sealed and movable connection with the scrubbing nozzle 14, the opening of the scrubbing nozzle 14 aligns with the mirror surface of the transparent lens protecting cover 5. A scrubbing control valve 13 is arranged on the expiratory air removal nozzle 15, the scrubbing control valve 13 is arranged on the laryngoscope handle 1, and the scrubbing control valve 13 is interlock control with the oxygen supply solenoid valve 12. When the scrubbing control valve 13 is opened, the oxygen supply solenoid valve 12 is closed, when the oxygen supply solenoid valve 12 is opened, the scrubbing control valve 13 is closed.

Figure 10:
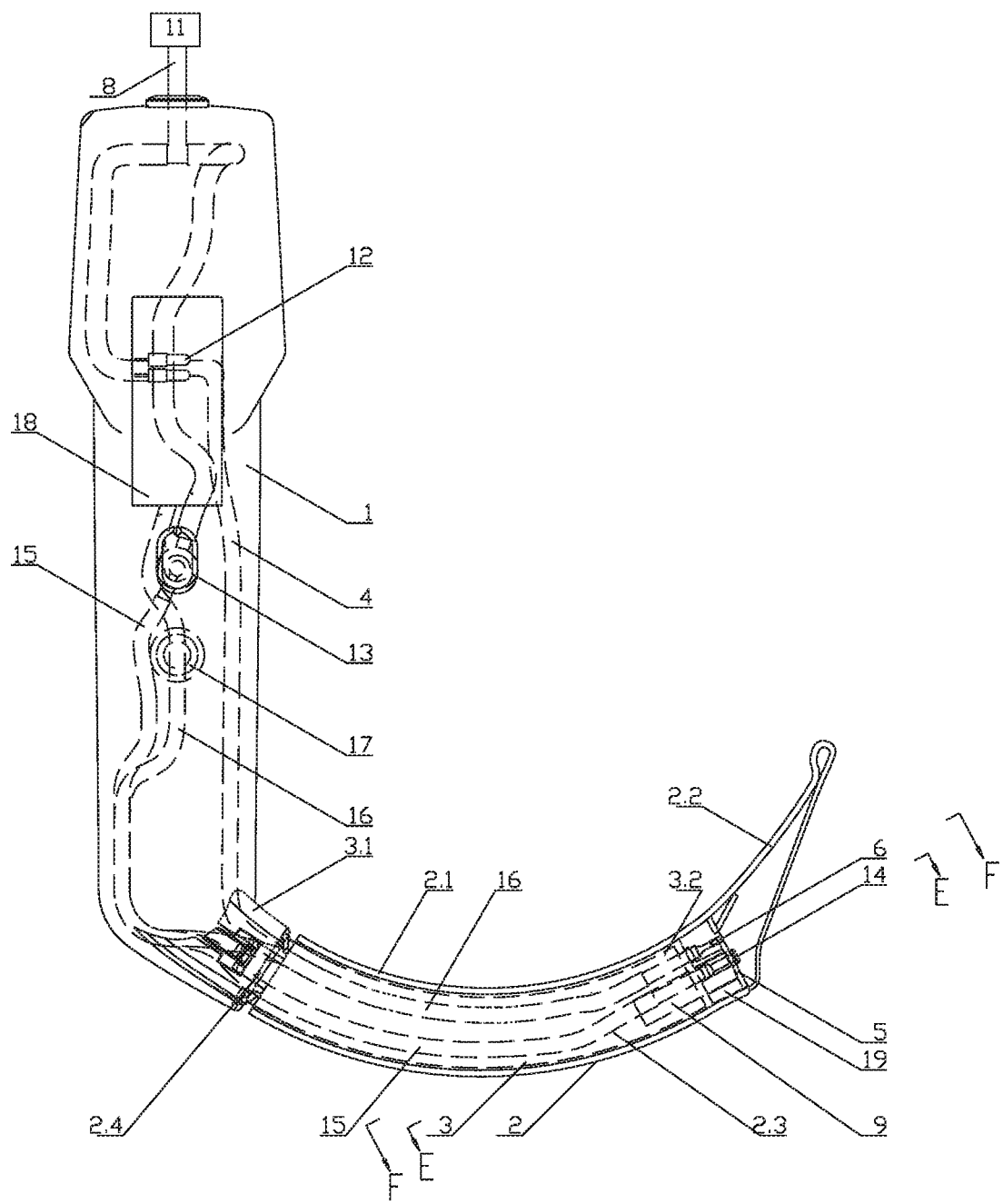
FIG. 10 shows the schematic diagram for the whole structure of the ventilatory laryngoscope with disposable laryngoscope lens having scrubbing function according to Embodiment 3.
Figure 11:
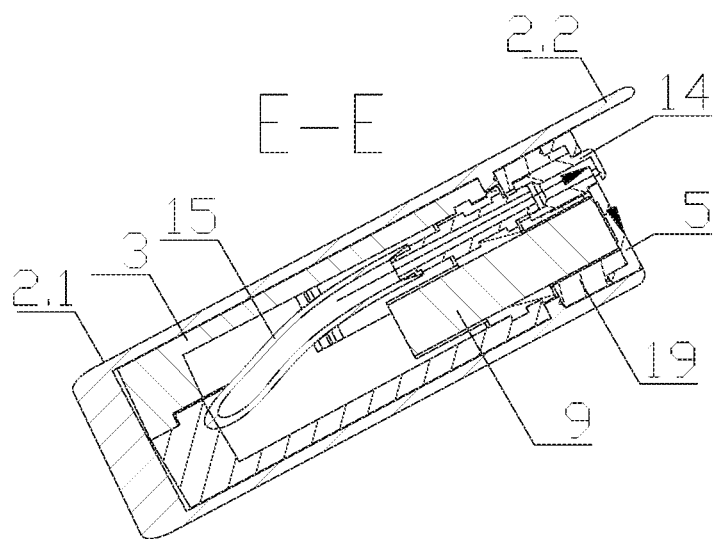
FIG. 11 shows the schematic diagram for section E-E shown in FIG. 10.
Figure 12:
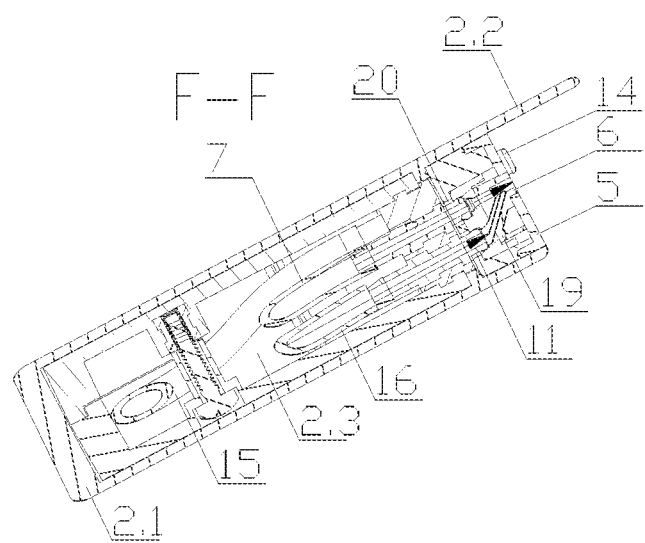
FIG. 12 shows the schematic diagram for section F-F shown in FIG. 10.
Figure 13:
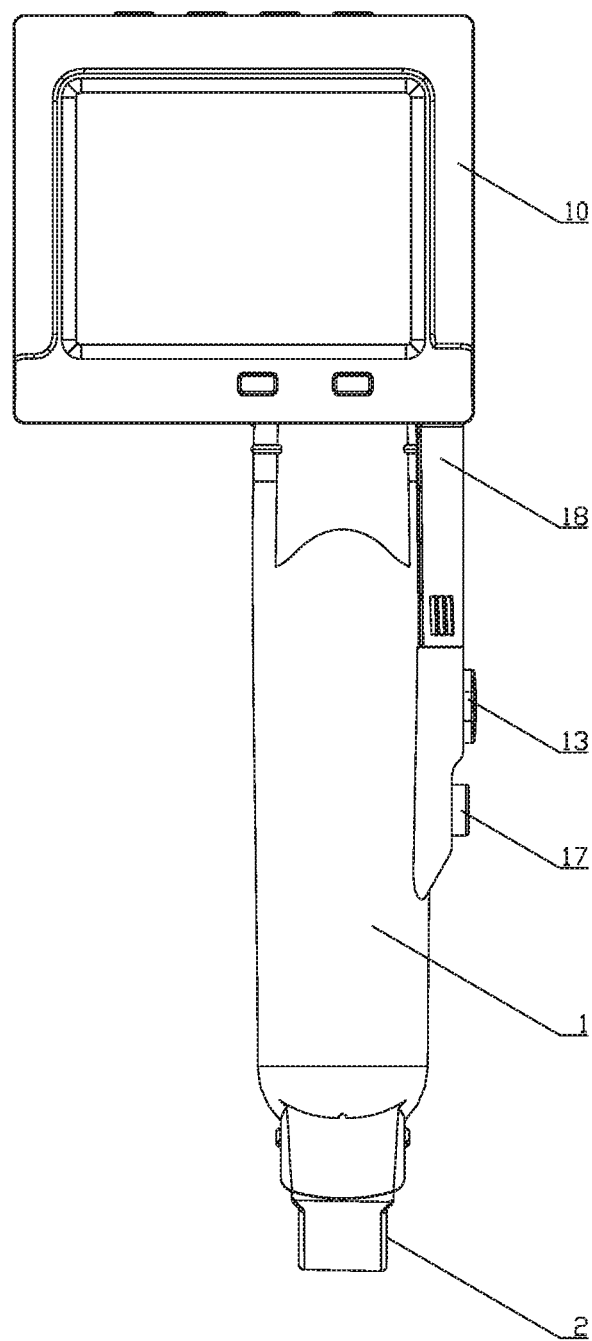
FIG. 13 shows the schematic diagram for the whole structure of the drug-delivering ventilatory video laryngoscope with disposable laryngoscope lens having scrubbing function according to Embodiment 4.
Figure 14:
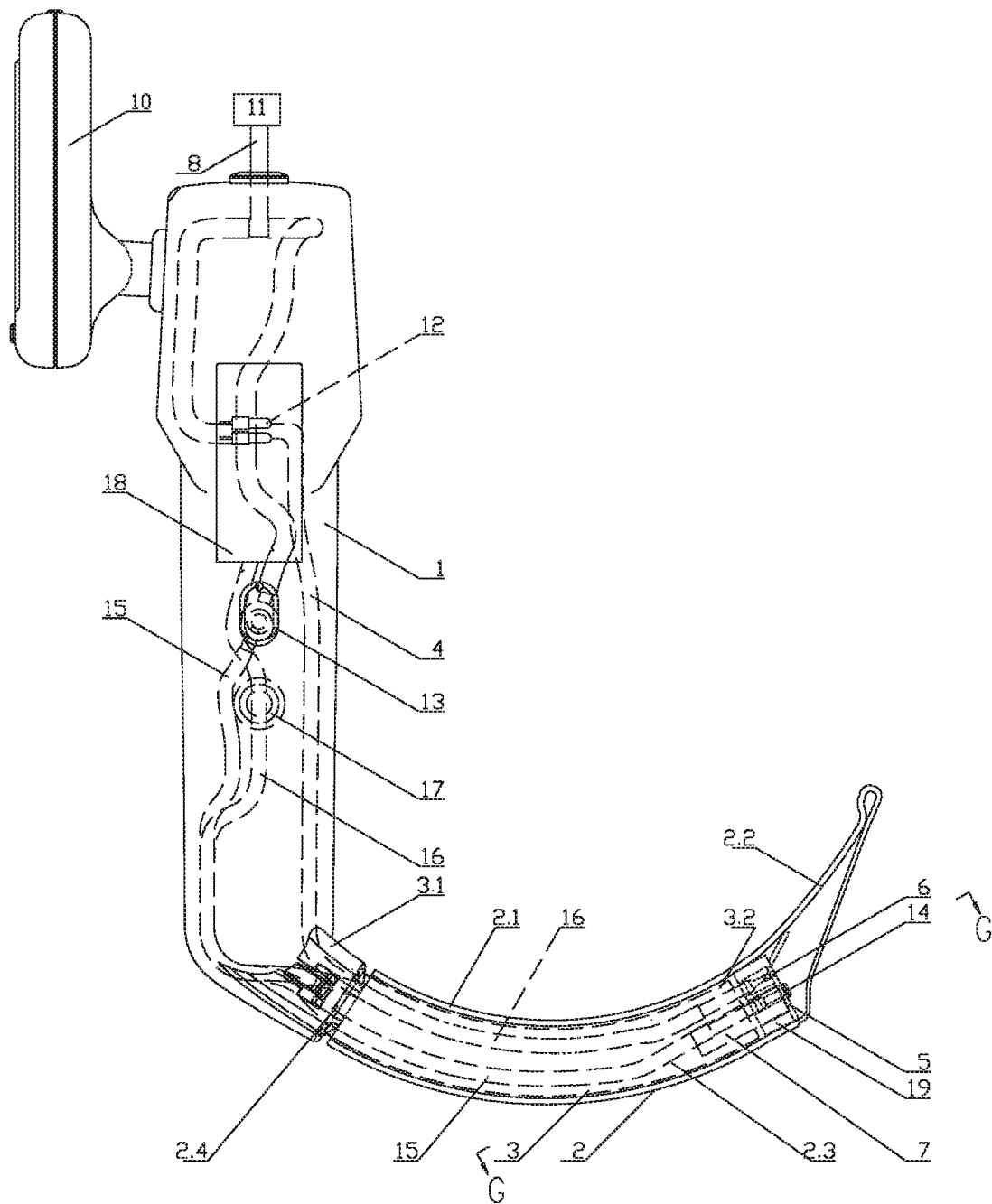
FIG. 14 shows the right side view of FIG. 13.
Figure 15:
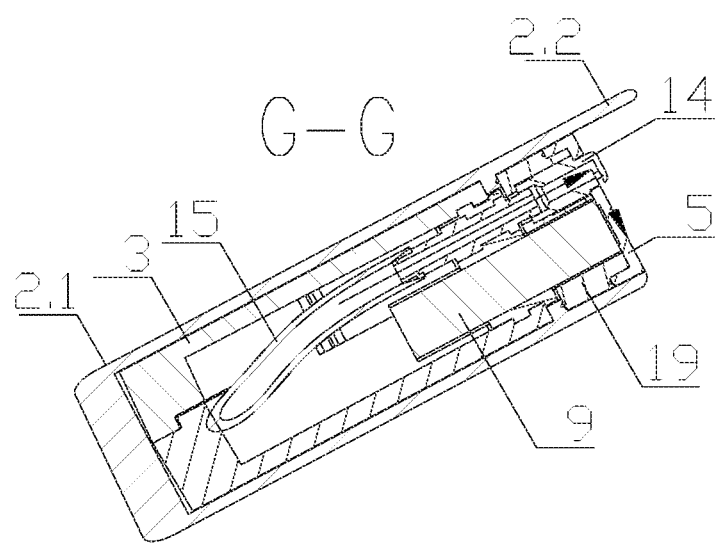
FIG. 15 shows the schematic diagram for section G-G shown in FIG. 14.
Figure 16:
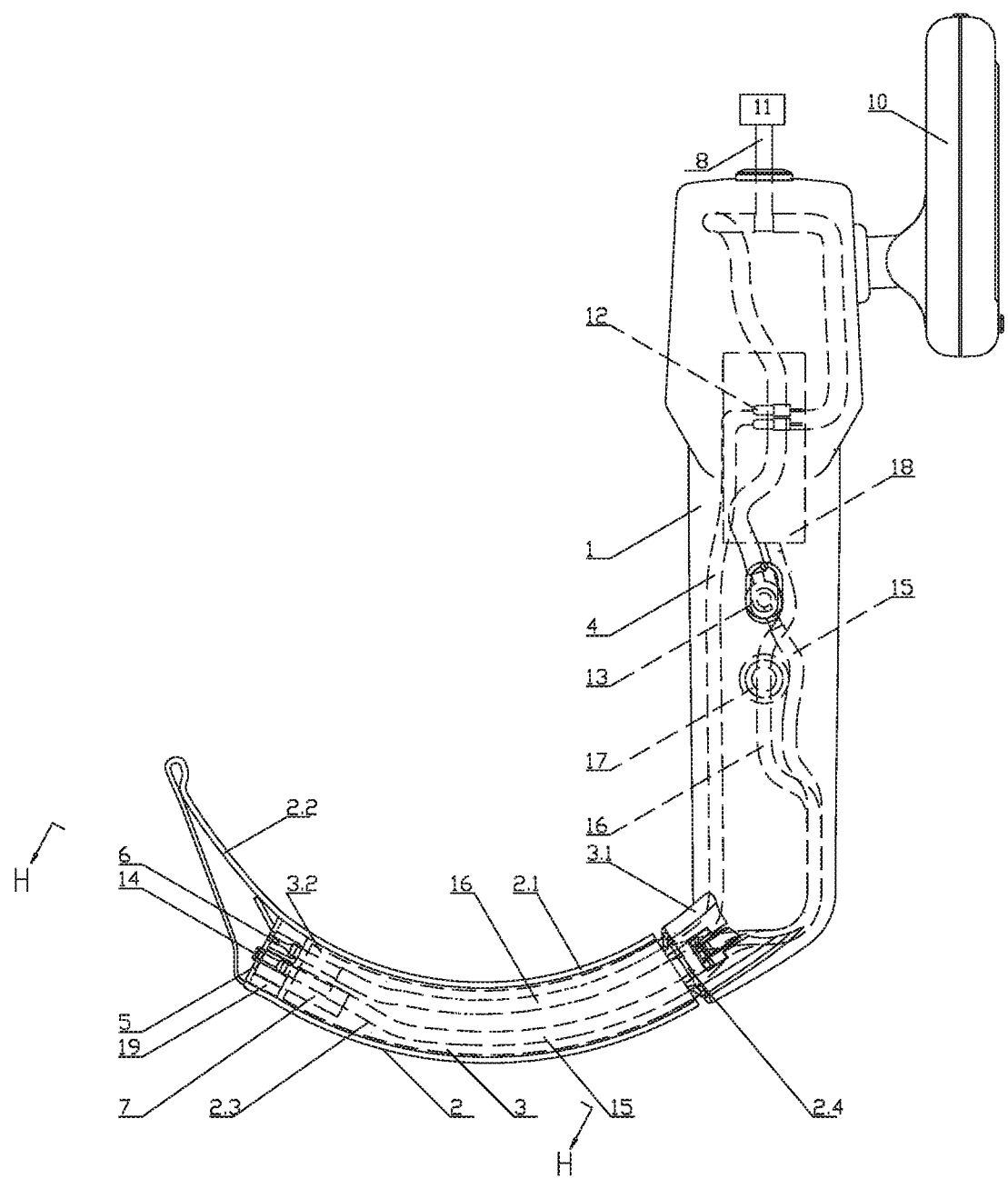
FIG. 16 shows the left side view of FIG. 13.
Figure 17:
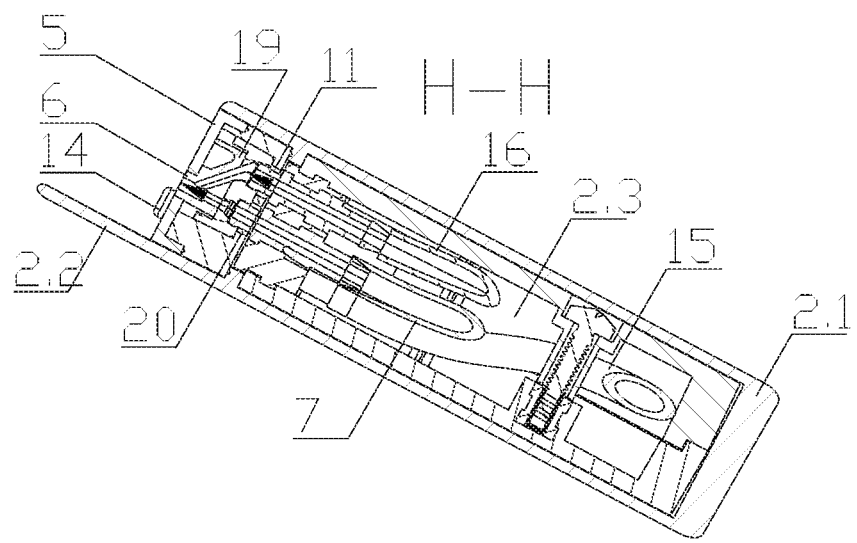
FIG. 17 shows the schematic diagram for section H-H shown in FIG. 14.

Embodiment 3: as shown in FIGS. 10-12, the drug-delivering ventilatory laryngoscope with disposable laryngoscope lens with scrubbing function, other structure of which is shown in Embodiment 2, further comprises a drug delivery pipe 16, a drug delivery control valve 17 is installed on the drug delivery pipe 16, the drug delivery control valve 17 is arranged on the laryngoscope handle 1, one end of the drug delivery pipe 16 is connected with a drug barrel 18 in the laryngoscope handle 1, and another end of the drug delivery pipe 16 is fixed on the top 3.2 of the extension arm 3 along the tail end of the extension arm 3; a atomizer head 19 is arranged on the transparent lens protecting cover 5, an air inlet 20 and a drug inlet 21 on the atomizer head 19 are respectively in sealed and movable connection with the drug delivery pipe 16 and the oxygen supply pipe 4 fixed on the top 3.2 of the extension arm. The drug delivery control valve 17 and the oxygen supply solenoid valve 12 are separately controlled.

Embodiment 4

FIGS. 13-17 shows a drug-delivering ventilatory video laryngoscope with disposable laryngoscope lens having scrubbing function, the other structure of which is shown in Embodiment 3. A display screen 10 is arranged on the laryngoscope handle 1, a camera 7 electrically connected with the display screen 10 is arranged on the top 3.2 of the extension arm, and the camera 7 is installed on the inner side of the transparent lens protecting cover 5.

The invention claimed is:

1. A ventilatory laryngoscope comprising:

a laryngoscope handle; and a laryngoscope lens movably connected with an extension arm disposed on an end of the laryngoscope handle, the extension arm being arranged in a laryngoscope lens cavity, wherein:

a transparent lens protecting cover is arranged on an end surface of a closed end of a front end of the laryngoscope lens cavity, an oxygen injecting through-hole is formed on the transparent lens protecting cover, an oxygen supply pipe extends from the laryngoscope handle cavity to a tail end of the extension arm along a top of the laryngoscope handle, and the oxygen supply pipe is fixed on a top of the extension arm from the tail end of the extension arm to the extension arm cavity, and in seal plug connection with the oxygen injecting through-hole, or the oxygen supply pipe is fixed from the extension arm cavity to the top of the extension arm along the tail end of the extension arm, and in seal plug connection with the oxygen injecting through-hole, and another end of the oxygen supply pipe is connected with or inserted into an oxygen source pipe.

2. The laryngoscope according to claim 1, the laryngoscope further comprising:

a disposable laryngoscope lens body; and
a tongue depressor; wherein
the laryngoscope lens body is straight or bent,
a fixing lug or a buckle is arranged on a tail end of the laryngoscope lens body, the fixing lug or the buckle being movably buckled with a slot of the tail end of the extension arm,
the tongue depressor is connected with a front end of the laryngoscope lens body,
the laryngoscope lens cavity is located in the laryngoscope lens body, and
an end port of a tail end of the laryngoscope lens cavity is open, and an end port of a front end of the laryngoscope lens cavity is closed, and the transparent lens protecting cover is arranged on an end surface of the closed end port of the front end of the laryngoscope lens cavity.

3. The laryngoscope according to claim 1, wherein a light source is arranged on the top of the extension arm, and the light source is arranged on an inner side of the transparent lens protecting cover.

4. The laryngoscope according to claim 3, further comprising
a drug delivery pipe;
a drug delivery control valve installed on the drug delivery pipe, the drug delivery control valve being arranged on the laryngoscope handle, one end of the drug delivery pipe being connected with a drug barrel in the laryngoscope handle, and another end of the drug delivery pipe is fixed on the top of the extension arm along the tail end of the extension arm; and
an atomizer head arranged on the transparent lens protecting cover, and an air inlet and a drug inlet on the atomizer head are respectively in sealed and movable connection with the drug delivery pipe and the oxygen supply pipe fixed on the top of the extension arm.

5. The laryngoscope according to claim 1, wherein an oxygen supply solenoid valve is arranged on the oxygen supply pipe in the laryngoscope handle, or the oxygen supply solenoid valve is arranged on any part of the oxygen source pipe.

6. The laryngoscope according to claim 1, further comprising:
a display screen arranged on the laryngoscope handle, and
a camera electrically connected with the display screen arranged on the top of the extension arm, and the camera is installed on an inner side of the transparent lens protecting cover.

7. The laryngoscope according to claim 1, further comprising:
a scrubbing nozzle arranged on the transparent lens protecting cover; and
an expiratory air removal nozzle arranged in the laryngoscope handle, one end of the expiratory air removal nozzle is connected with an oxygen source, another end of the expiratory air removal nozzle is inserted and fixed on the top of the extension arm, and in sealed and movable connection with the scrubbing nozzle, and an opening of the scrubbing nozzle aligns with the mirror surface of the transparent lens protecting cover.

8. The laryngoscope according to claim 1, further comprising:
a drug delivery pipe;
a drug delivery control valve installed on the drug delivery pipe, the drug delivery control valve being arranged on the laryngoscope handle, one end of the drug delivery pipe is connected with a drug barrel in the laryngoscope handle, and another end of the drug delivery pipe is fixed on the top of the extension arm along the tail end of the extension arm; and
an atomizer head arranged on the transparent lens protecting cover, and an air inlet and a drug inlet on the atomizer head are respectively in sealed and movable connection with the drug delivery pipe and the oxygen supply pipe fixed on the top of the extension arm.

9. A ventilatory laryngoscope with disposable laryngoscope lens having scrubbing function, the ventilatory laryngoscope comprising:
a laryngoscope handle; and
a laryngoscope lens movably connected with an extension arm disposed on an end of the laryngoscope handle, the extension arm being arranged in a laryngoscope lens cavity, wherein:
a transparent lens protecting cover is arranged on an end surface of a closed end of a front end of the laryngoscope lens cavity,
an oxygen injecting through-hole is formed on the transparent lens protecting cover,
an oxygen supply pipe extends from the laryngoscope handle cavity to a tail end of the extension arm along a top of the laryngoscope handle,
the oxygen supply pipe is fixed on a top of the extension arm from the tail end of the extension arm to the extension arm cavity, and in seal plug connection with the oxygen injecting through-hole, or the oxygen supply pipe is fixed from the extension arm cavity to the top of the extension arm along the tail end of the extension arm, and in seal plug connection with the oxygen injecting through-hole, and another end of the oxygen supply pipe is connected with or inserted into an oxygen source pipe,
a scrubbing nozzle is arranged on the transparent lens protecting cover, and
an expiratory air removal nozzle is arranged in the laryngoscope handle, a first end of the expiratory air removal nozzle is connected with an oxygen source, a second end of the expiratory air removal nozzle is inserted and fixed on the top of the extension arm, and in sealed and movable connection with the scrubbing nozzle, an opening of the scrubbing nozzle aligns with a mirror surface of the transparent lens protecting cover.

10. The laryngoscope according to claim 9, further comprising a scrubbing control valve arranged on the expiratory air removal nozzle, the scrubbing control valve being arranged on the laryngoscope handle, and the scrubbing control valve is in interlock control with an oxygen supply solenoid valve, wherein when the scrubbing control valve is opened, the oxygen supply solenoid valve is closed, and when the oxygen supply solenoid valve is opened, the scrubbing control valve is closed.

11. A drug-delivering ventilatory laryngoscope with disposable laryngoscope lens having scrubbing function, the ventilatory laryngoscope comprising:
a laryngoscope handle; and
a laryngoscope lens movably connected with an extension arm disposed on an end of the laryngoscope handle, the extension arm being arranged in a laryngoscope lens cavity, wherein:
a transparent lens protecting cover is arranged on an end surface of a closed end of a front end of the laryngoscope lens cavity,
an oxygen injecting through-hole is formed on the transparent lens protecting cover, an oxygen supply pipe extends from the laryngoscope handle cavity to a tail end of the extension arm along a top of the laryngoscope handle, the oxygen supply pipe being fixed on a top of the extension arm from the tail end of the extension arm to the extension arm cavity, and in seal plug connection with the oxygen injecting through-hole, or the oxygen supply pipe is fixed from the extension arm cavity to the top of the extension arm along the tail end of the extension arm, and in seal plug connection with the oxygen injecting through-hole, and another end of the oxygen supply pipe is connected with or inserted into an oxygen source pipe, a scrubbing nozzle is arranged on the transparent lens protecting cover, an expiratory air removal nozzle is arranged in the laryngoscope handle, one end of the expiratory air removal nozzle is connected with an oxygen source, another end of the expiratory air removal nozzle is inserted and fixed on the top of the extension arm, and in sealed and movable connection with the scrubbing nozzle, and an opening of the scrubbing nozzle aligns with a mirror surface of the transparent lens protecting cover, a drug delivery pipe, where a drug delivery control valve is installed on the drug delivery pipe, is arranged on the laryngoscope handle, one end of the drug delivery pipe is connected with a drug barrel in the laryngoscope handle, and another end of the drug delivery pipe is fixed on the top of the extension arm along the tail end of the extension arm, and an atomizer head is arranged on the transparent lens protecting cover, an air inlet and a drug inlet on the atomizer head are respectively in sealed and movable connection with the drug delivery pipe and the oxygen supply pipe fixed on the top of the extension arm.

12. A drug-delivering ventilatory video laryngoscope with disposable laryngoscope lens having scrubbing function, the ventilatory video laryngoscope comprising:

a laryngoscope handle; and a laryngoscope lens movably connected with an extension arm on an end of the laryngoscope handle, the extension arm being arranged in a laryngoscope lens cavity, wherein:

a transparent lens protecting cover is arranged on an end surface of a closed end of a front end of the laryngoscope lens cavity, an oxygen injecting through-hole is formed on the transparent lens protecting cover, an oxygen supply pipe extends from the laryngoscope handle cavity to a tail end of the extension arm along a top of the laryngoscope handle, the oxygen supply pipe being fixed on a top of the extension arm from the tail end of the extension arm to the extension arm cavity, and in seal plug connection with the oxygen injecting through-hole, or the oxygen supply pipe being fixed from the extension arm cavity to the top of the extension arm along the tail end of the extension arm, and in seal plug connection with the oxygen injecting through-hole, and another end of the oxygen supply pipe is connected with or inserted into an oxygen source pipe, a scrubbing nozzle is arranged on the transparent lens protecting cover, an expiratory air removal nozzle is arranged in the laryngoscope handle, one end of the expiratory air removal nozzle is connected with an oxygen source, another end of the expiratory air removal nozzle is inserted and fixed on the top of the extension arm, and in sealed and movable connection with the scrubbing nozzle, and an opening of the scrubbing nozzle aligns with a mirror surface of the transparent lens protecting cover, a drug delivery pipe, where a drug delivery control valve is installed on the drug delivery pipe, is arranged on the laryngoscope handle, one end of the drug delivery pipe is connected with a drug barrel in the laryngoscope handle, and another end of the drug delivery pipe is fixed on the top of the extension arm along the tail end of the extension pipe, an atomizer head is arranged on the transparent lens protecting cover, an air inlet and a drug inlet on the atomizer head being respectively in sealed and movable connection with the drug delivery pipe and the oxygen supply pipe fixed on the top of the extension arm, and a display screen is arranged on the laryngoscope handle, a camera electrically connected with the display screen is arranged on the top of the extension arm, and the camera is installed on an inner side of the transparent lens protecting cover.

* * * * *